US012799171B2

(12) United States Patent
Zhu et al.

(10) Patent No.: US 12,799,171 B2
(45) Date of Patent: Nov. 17, 2026

(54) SWEET PROTEIN MUTANTS, PREPARATION METHODS, AND USE THEREOF

(71) Applicants: KINGDOMWAY BIOTECHNOLOGY (JIANGSU) CO., LTD., Nantong (CN); INNER MONGOLIA KINGDOMWAY PHARMACEUTICAL CO., LTD., Huhhot (CN); XIAMEN KINGDOMWAY GROUP COMPANY, Xiamen (CN)

(72) Inventors: Jun Zhu, Nantong (CN); Fei Xu, Nantong (CN); Xingyi Zhang, Nantong (CN); Deyao Meng, Nantong (CN); Dan Li, Xiamen (CN); Faguang Liu, Nantong (CN)

(73) Assignees: KINGDOMWAY BIOTECHNOLOGY (JIANGSU) CO., LTD., Nantong (CN); INNER MONGOLIA KINGDOMWAY PHARMACEUTICAL CO., LTD., Huhhot (CN); XIAMEN KINGDOMWAY GROUP COMPANY, Xiamen (CN)

( * ) Notice: Subject to any disclaimer, the term of this patent is extended or adjusted under 35 U.S.C. 154(b) by 0 days.

(21) Appl. No.: 19/565,562

(22) Filed: Mar. 13, 2026

(65) Prior Publication Data

US 2026/0184746 A1 Jul. 2, 2026

Related U.S. Application Data

(63) Continuation-in-part of application No. 19/214,031, filed on May 20, 2025, now abandoned.

(30) Foreign Application Priority Data

Dec. 31, 2024 (CN) ......................... 202411987663.7

(51) Int. Cl.
*C07K 14/415* (2006.01)
*C07K 1/34* (2006.01)
(Continued)

(52) U.S. Cl.
CPC .............. *C07K 14/415* (2013.01); *C07K 1/34* (2013.01); *C07K 14/43* (2013.01); *C12N 15/11* (2013.01); *C12N 15/815* (2013.01)

(58) Field of Classification Search
None
See application file for complete search history.

(56) References Cited

U.S. PATENT DOCUMENTS

2017/0143024 A1* 5/2017 Kwang ..................... A23J 3/14

FOREIGN PATENT DOCUMENTS

CN 116333080 A 6/2023
CN 119192319 A 12/2024
(Continued)

OTHER PUBLICATIONS

Zheng, Weiwei, Molecular Construction of the New Sweet Protein Brazzein Mutant, Master's Electronic Journal Engineering and Technology Series I, 2018, 155 pages.

*Primary Examiner* — Suzanne M Noakes
*Assistant Examiner* — Qing Xu
(74) *Attorney, Agent, or Firm* — METIS IP LLC

(57) ABSTRACT

Brazzein mutants, preparation methods, and use thereof are provided. The brazzein mutants are derived from a wild type brazzein having an amino acid sequence set forth in SEQ ID NO. 1, the mutation including amino acid mutations relative
(Continued)

to SEQ ID NO: 1 selected from at least one of K5D, V7R, D29N, A32K, N44E, and E53R.

19 Claims, 14 Drawing Sheets

Specification includes a Sequence Listing.

(51) Int. Cl.
*C07K 14/43* (2006.01)
*C12N 15/11* (2006.01)
*C12N 15/81* (2006.01)

(56) References Cited

FOREIGN PATENT DOCUMENTS

| | | | | |
|---|---|---|---|---|
| KR | 20090050525 | A | * | 5/2009 |
| WO | WO 2025/147505 | A1 | * | 7/2025 |

* cited by examiner

WT

K5D+V7R+
A32K+N44E

D29N+A32K+
N44E+E53R

SEQUENCE LISTING

```
Sequence total quantity: 38
SEQ ID NO: 1            moltype = AA  length = 54
FEATURE                 Location/Qualifiers
source                  1..54
                        mol_type = protein
                        organism = unidentified
SEQUENCE: 1
QDKCKKVYEN YPVSKCQLAN QCNYDCKLDK HARSGECFYD EKRNLQCICD YCEY        54

SEQ ID NO: 2            moltype = DNA  length = 165
FEATURE                 Location/Qualifiers
source                  1..165
                        mol_type = other DNA
                        organism = unidentified
SEQUENCE: 2
caggacaagt gcaagaaggt ctacgagaac tacccagttt ccaagtgcca gttggctaac  60
cagtgtaact acgactgcaa gttggacaag cacgctagat ctggtgagtg tttctacgac  120
gagaagagaa acctgcagtg catctgtgac tactgcgagt actaa                  165

SEQ ID NO: 3            moltype = DNA  length = 40
FEATURE                 Location/Qualifiers
source                  1..40
                        mol_type = other DNA
```

```
                        organism = synthetic construct
SEQUENCE: 3
gaaaagacag gacaagtgcg acaaggtcta cgagaactac                         40

SEQ ID NO: 4            moltype = DNA  length = 40
FEATURE                 Location/Qualifiers
source                  1..40
                        mol_type = other DNA
                        organism = synthetic construct
SEQUENCE: 4
gtagttctcg tagaccttgt cgcacttgtc ctgtcttttc                         40

SEQ ID NO: 5            moltype = DNA  length = 31
FEATURE                 Location/Qualifiers
source                  1..31
                        mol_type = other DNA
                        organism = synthetic construct
SEQUENCE: 5
gacaagtgca agaagcgcta cgagaactac c                                  31

SEQ ID NO: 6            moltype = DNA  length = 31
FEATURE                 Location/Qualifiers
source                  1..31
                        mol_type = other DNA
                        organism = synthetic construct
SEQUENCE: 6
ggtagttctc gtagcgcttc ttgcacttgt c                                  31

SEQ ID NO: 7            moltype = DNA  length = 33
FEATURE                 Location/Qualifiers
source                  1..33
                        mol_type = other DNA
                        organism = synthetic construct
SEQUENCE: 7
ctacgactgc aagttgaaca agcacgctag atc                                33

SEQ ID NO: 8            moltype = DNA  length = 33
FEATURE                 Location/Qualifiers
source                  1..33
                        mol_type = other DNA
                        organism = synthetic construct
SEQUENCE: 8
gatctagcgt gcttgttcaa cttgcagtcg tag                                33

SEQ ID NO: 9            moltype = DNA  length = 27
FEATURE                 Location/Qualifiers
source                  1..27
                        mol_type = other DNA
                        organism = synthetic construct
SEQUENCE: 9
atctgtgact actgcagata ctaagcg                                       27

SEQ ID NO: 10           moltype = DNA  length = 27
FEATURE                 Location/Qualifiers
source                  1..27
                        mol_type = other DNA
                        organism = synthetic construct
SEQUENCE: 10
tctgcagtag tcacagatgc actgcag                                       27

SEQ ID NO: 11           moltype = AA  length = 54
FEATURE                 Location/Qualifiers
source                  1..54
                        mol_type = protein
                        organism = synthetic construct
SEQUENCE: 11
QDKCDKVYEN YPVSKCQLAN QCNYDCKLDK HARSGECFYD EKRNLQCICD YCEY         54

SEQ ID NO: 12           moltype = DNA  length = 165
FEATURE                 Location/Qualifiers
source                  1..165
                        mol_type = other DNA
                        organism = synthetic construct
SEQUENCE: 12
caggacaagt gcgacaaggt ctacgagaac tacccagttt ccaagtgcca gttggctaac  60
cagtgtaact acgactgcaa gttggacaag cacgctagat ctggtgagtg tttctacgac  120
gagaagagaa acctgcagtg catctgtgac tactgcgagt actaa                   165

SEQ ID NO: 13           moltype = AA  length = 54
```

```
FEATURE                Location/Qualifiers
source                 1..54
                       mol_type = protein
                       organism = synthetic construct
SEQUENCE: 13
QDKCKKRYEN YPVSKCQLAN QCNYDCKLDK HARSGECFYD EKRNLQCICD YCEY        54

SEQ ID NO: 14          moltype = DNA  length = 165
FEATURE                Location/Qualifiers
source                 1..165
                       mol_type = other DNA
                       organism = synthetic construct
SEQUENCE: 14
caggacaagt gcaagaagcg ctacgagaac tacccagttt ccaagtgcca gttggctaac  60
cagtgtaact acgactgcaa gttggacaag cacgctagat ctggtgagtg tttctacgac  120
gagaagagaa acctgcagtg catctgtgac tactgcgagt actaa                  165

SEQ ID NO: 15          moltype = AA  length = 54
FEATURE                Location/Qualifiers
source                 1..54
                       mol_type = protein
                       organism = synthetic construct
SEQUENCE: 15
QDKCKKVYEN YPVSKCQLAN QCNYDCKLNK HARSGECFYD EKRNLQCICD YCEY        54

SEQ ID NO: 16          moltype = DNA  length = 165
FEATURE                Location/Qualifiers
source                 1..165
                       mol_type = other DNA
                       organism = synthetic construct
SEQUENCE: 16
caggacaagt gcaagaaggt ctacgagaac tacccagttt ccaagtgcca gttggctaac  60
cagtgtaact acgactgcaa gttgaacaag cacgctagat ctggtgagtg tttctacgac  120
gagaagagaa acctgcagtg catctgtgac tactgcgagt actaa                  165

SEQ ID NO: 17          moltype = AA  length = 54
FEATURE                Location/Qualifiers
source                 1..54
                       mol_type = protein
                       organism = synthetic construct
SEQUENCE: 17
QDKCKKVYEN YPVSKCQLAN QCNYDCKLDK HARSGECFYD EKRNLQCICD YCRY        54

SEQ ID NO: 18          moltype = DNA  length = 165
FEATURE                Location/Qualifiers
source                 1..165
                       mol_type = other DNA
                       organism = synthetic construct
SEQUENCE: 18
caggacaagt gcaagaaggt ctacgagaac tacccagttt ccaagtgcca gttggctaac  60
cagtgtaact acgactgcaa gttggacaag cacgctagat ctggtgagtg tttctacgac  120
gagaagagaa acctgcagtg catctgtgac tactgcagat actaa                  165

SEQ ID NO: 19          moltype = AA  length = 54
FEATURE                Location/Qualifiers
source                 1..54
                       mol_type = protein
                       organism = synthetic construct
SEQUENCE: 19
QDKCDKRYEN YPVSKCQLAN QCNYDCKLDK HARSGECFYD EKRNLQCICD YCEY        54

SEQ ID NO: 20          moltype = DNA  length = 165
FEATURE                Location/Qualifiers
source                 1..165
                       mol_type = other DNA
                       organism = synthetic construct
SEQUENCE: 20
caggacaagt gcgacaagcg ctacgagaac tacccagttt ccaagtgcca gttggctaac  60
cagtgtaact acgactgcaa gttggacaag cacgctagat ctggtgagtg tttctacgac  120
gagaagagaa acctgcagtg catctgtgac tactgcgagt actaa                  165

SEQ ID NO: 21          moltype = AA  length = 54
FEATURE                Location/Qualifiers
source                 1..54
                       mol_type = protein
                       organism = synthetic construct
SEQUENCE: 21
QDKCKKVYEN YPVSKCQLAN QCNYDCKLNK HARSGECFYD EKRNLQCICD YCRY        54
```

```
SEQ ID NO: 22          moltype = DNA  length = 165
FEATURE                Location/Qualifiers
source                 1..165
                       mol_type = other DNA
                       organism = synthetic construct
SEQUENCE: 22
caggacaagt gcaagaaggt ctacgagaac tacccagttt ccaagtgcca gttggctaac  60
cagtgtaact acgactgcaa gttgaacaag cacgctagat ctggtgagtg tttctacgac  120
gagaagagaa acctgcagtg catctgtgac tactgcagat actaa                  165

SEQ ID NO: 23          moltype = AA  length = 54
FEATURE                Location/Qualifiers
source                 1..54
                       mol_type = protein
                       organism = synthetic construct
SEQUENCE: 23
QDKCDKRYEN YPVSKCQLAN QCNYDCKLNK HARSGECFYD EKRNLQCICD YCRY        54

SEQ ID NO: 24          moltype = DNA  length = 165
FEATURE                Location/Qualifiers
source                 1..165
                       mol_type = other DNA
                       organism = synthetic construct
SEQUENCE: 24
caggacaagt gcgacaagcg ctacgagaac tacccagttt ccaagtgcca gttggctaac  60
cagtgtaact acgactgcaa gttgaacaag cacgctagat ctggtgagtg tttctacgac  120
gagaagagaa acctgcagtg catctgtgac tactgcagat actaa                  165

SEQ ID NO: 25          moltype = AA  length = 54
FEATURE                Location/Qualifiers
source                 1..54
                       mol_type = protein
                       organism = synthetic construct
SEQUENCE: 25
QDKCKKVYEN YPVSKCQLAN QCNYDCKLDK HKRSGECFYD EKRNLQCICD YCEY        54

SEQ ID NO: 26          moltype = DNA  length = 165
FEATURE                Location/Qualifiers
source                 1..165
                       mol_type = other DNA
                       organism = synthetic construct
SEQUENCE: 26
caggacaagt gcaagaaggt ctacgagaac tacccagttt ccaagtgcca gttggctaac  60
cagtgtaact acgactgcaa gttggacaag cacaagagat ctggtgagtg tttctacgac  120
gagaagagaa acctgcagtg catctgtgac tactgcgagt actaa                  165

SEQ ID NO: 27          moltype = AA  length = 54
FEATURE                Location/Qualifiers
source                 1..54
                       mol_type = protein
                       organism = synthetic construct
SEQUENCE: 27
QDKCKKVYEN YPVSKCQLAN QCNYDCKLDK HARSGECFYD EKRELQCICD YCEY        54

SEQ ID NO: 28          moltype = DNA  length = 165
FEATURE                Location/Qualifiers
source                 1..165
                       mol_type = other DNA
                       organism = synthetic construct
SEQUENCE: 28
caggacaagt gcaagaaggt ctacgagaac tacccagttt ccaagtgcca gttggctaac  60
cagtgtaact acgactgcaa gttggacaag cacgctagat ctggtgagtg tttctacgac  120
gagaagagag agctgcagtg catctgtgac tactgcgagt actaa                  165

SEQ ID NO: 29          moltype = AA  length = 54
FEATURE                Location/Qualifiers
source                 1..54
                       mol_type = protein
                       organism = synthetic construct
SEQUENCE: 29
QDKCDKRYEN YPVSKCQLAN QCNYDCKLDK HKRSGECFYD EKRELQCICD YCEY        54

SEQ ID NO: 30          moltype = DNA  length = 165
FEATURE                Location/Qualifiers
source                 1..165
                       mol_type = other DNA
                       organism = synthetic construct
SEQUENCE: 30
caggacaagt gcgacaagcg ctacgagaac tacccagttt ccaagtgcca gttggctaac  60
```

```
cagtgtaact acgactgcaa gttggacaag cacaagagat ctggtgagtg tttctacgac  120
gagaagagag agctgcagtg catctgtgac tactgcgagt actaa                  165

SEQ ID NO: 31          moltype = AA  length = 54
FEATURE                Location/Qualifiers
source                 1..54
                       mol_type = protein
                       organism = synthetic construct
SEQUENCE: 31
QDKCKKVYEN YPVSKCQLAN QCNYDCKLNK HKRSGECFYD EKRELQCICD YCRY        54

SEQ ID NO: 32          moltype = DNA  length = 165
FEATURE                Location/Qualifiers
source                 1..165
                       mol_type = other DNA
                       organism = synthetic construct
SEQUENCE: 32
caggacaagt gcaagaaggt ctacgagaac tacccagttt ccaagtgcca gttggctaac  60
cagtgtaact acgactgcaa gttgaacaag cacaagagat ctggtgagtg tttctacgac  120
gagaagagag agctgcagtg catctgtgac tactgcagat actaa                  165

SEQ ID NO: 33          moltype = AA  length = 54
FEATURE                Location/Qualifiers
source                 1..54
                       mol_type = protein
                       organism = synthetic construct
SEQUENCE: 33
QDKCDKRYEN YPVSKCQLAN QCNYDCKLNK HKRSGECFYD EKRELQCICD YCRY        54

SEQ ID NO: 34          moltype = DNA  length = 165
FEATURE                Location/Qualifiers
source                 1..165
                       mol_type = other DNA
                       organism = synthetic construct
SEQUENCE: 34
caggacaagt gcgacaagcg ctacgagaac tacccagttt ccaagtgcca gttggctaac  60
cagtgtaact acgactgcaa gttgaacaag cacaagagat ctggtgagtg tttctacgac  120
gagaagagag agctgcagtg catctgtgac tactgcagat actaa                  165

SEQ ID NO: 35          moltype = DNA  length = 38
FEATURE                Location/Qualifiers
source                 1..38
                       mol_type = other DNA
                       organism = synthetic construct
SEQUENCE: 35
gcaagttgga caagcacaag agatctggtg agtgtttc                          38

SEQ ID NO: 36          moltype = DNA  length = 38
FEATURE                Location/Qualifiers
source                 1..38
                       mol_type = other DNA
                       organism = synthetic construct
SEQUENCE: 36
gaaacactca ccagatctct tgtgcttgtc caacttgc                          38

SEQ ID NO: 37          moltype = DNA  length = 35
FEATURE                Location/Qualifiers
source                 1..35
                       mol_type = other DNA
                       organism = synthetic construct
SEQUENCE: 37
ctacgacgag aagagagagc tgcagtgcat ctgtg                             35

SEQ ID NO: 38          moltype = DNA  length = 35
FEATURE                Location/Qualifiers
source                 1..35
                       mol_type = other DNA
                       organism = synthetic construct
SEQUENCE: 38
cacagatgca ctgcagctct ctcttctcgt cgtag                             35
```

SWEET PROTEIN MUTANTS, PREPARATION METHODS, AND USE THEREOF

CROSS-REFERENCE TO RELATED APPLICATIONS

This application is a continuation-in-part application of U.S. patent application Ser. No. 19/214,031 filed on May 20, 2025, which claims priority to Chinese Patent Application No. 202411987663.7, filed on Dec. 31, 2024, the entire contents of each of which are incorporated herein by reference.

SEQUENCE LISTING

The instant application contains a Sequence Listing which is submitted electronically in XML format and is hereby incorporated by reference in its entirety. The XML copy, created on Mar. 4, 2026, is named "2026 Mar. 4-Sequence List-20605-0005US01," and is 36,988 bytes in size.

TECHNICAL FIELD

The present disclosure relates to the field of biotechnology, and in particular to a sweet protein mutant and a preparation method and use thereof.

BACKGROUND

The World Health Organization (WHO) indicates that excessive sugar intake is a significant inducement for chronic diseases such as obesity and diabetes. According to the standards announced by the WHO in 2019, the daily sugar intake for adults should not exceed 25 g. With the changes in people's living habits, the sugar substitute industry has gradually emerged, leading to the rise of suppliers specializing in "sugar-free products".

As a substitute for sugar, sweeteners have garnered much attention. In recent years, some companies have begun to focus on sweet proteins, a type of high-intensity, pure-tasting, and natural sweeteners free of side effects, which are expected to lead the future of the high-intensity sweetener industry. Due to its sugar-like taste and structural stability in a wide range of temperatures and pH, brazzein protein is considered as the most promising sweet protein among various sweet proteins. Brazzein protein is extracted from the fruit of the West African tropical plant *Pentadiplandra brazzeana* Baillon and it exhibits a sweetness intensity 500-2000 times that of the equal mass of sucrose. Compared with other sweet proteins, the brazzein protein has advantages of the smallest molecular weight, excellent water solubility, and retaining its sweetness after heat treatment at 80 °C for 4 h, demonstrating good thermal stability and pH stability.

However, the yield of the sweet protein derived from natural plants is relatively low, making it difficult to meet market demand. In addition, the sweet protein faces issues such as misfolding, tendency to form inclusion bodies, and insufficient expression in heterologous recombinant expression, which hinders its commercial production and application.

SUMMARY

One or more embodiments of the present disclosure provide a sweet protein mutant derived from a sweet protein having an amino acid sequence set forth in SEQ ID NO. 1, the mutant comprises amino acid mutations relative to SEQ ID NO: 1 selected from at least one of K5D, V7R, D29N, A32K, N44E, or E53R.

One or more embodiments of the present disclosure provide a nucleic acid molecule encoding the sweet protein mutant.

One or more embodiments of the present disclosure provide an expression vector comprising at least one copy of the nucleic acid molecule.

One or more embodiments of the present disclosure provide a sweet protein mutant transformant. The sweet protein mutant transformant is a genetically engineered strain that expresses the sweet protein mutant.

One or more embodiments of the present disclosure provide a preparation method for the sweet protein mutant. The preparation method comprises constructing an expression vector, the expression vector comprising at least one copy of a nucleic acid sequence that encodes the sweet protein mutant; constructing a sweet protein mutant transformant by transforming the expression vector into a recipient cell; and obtaining the sweet protein mutant by culturing the sweet protein mutant transformant and collecting a culture.

One or more embodiments of the present disclosure provide a purification method for the sweet protein mutant. The purification method comprises: culturing a sweet protein mutant transformant to collect a culture, separating and removing contaminating proteins from the culture and filtering, adsorbing the sweet protein mutant from a filtered solution through a cation exchange resin, followed by eluting to collect an eluent, performing nanofiltration on the eluent for desalination and concentration, and performing lyophilization on a nanofiltered eluent to obtain a purified sweet protein mutant, the sweet protein mutant transformant comprising a nucleic acid molecule encoding the sweet protein mutant.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
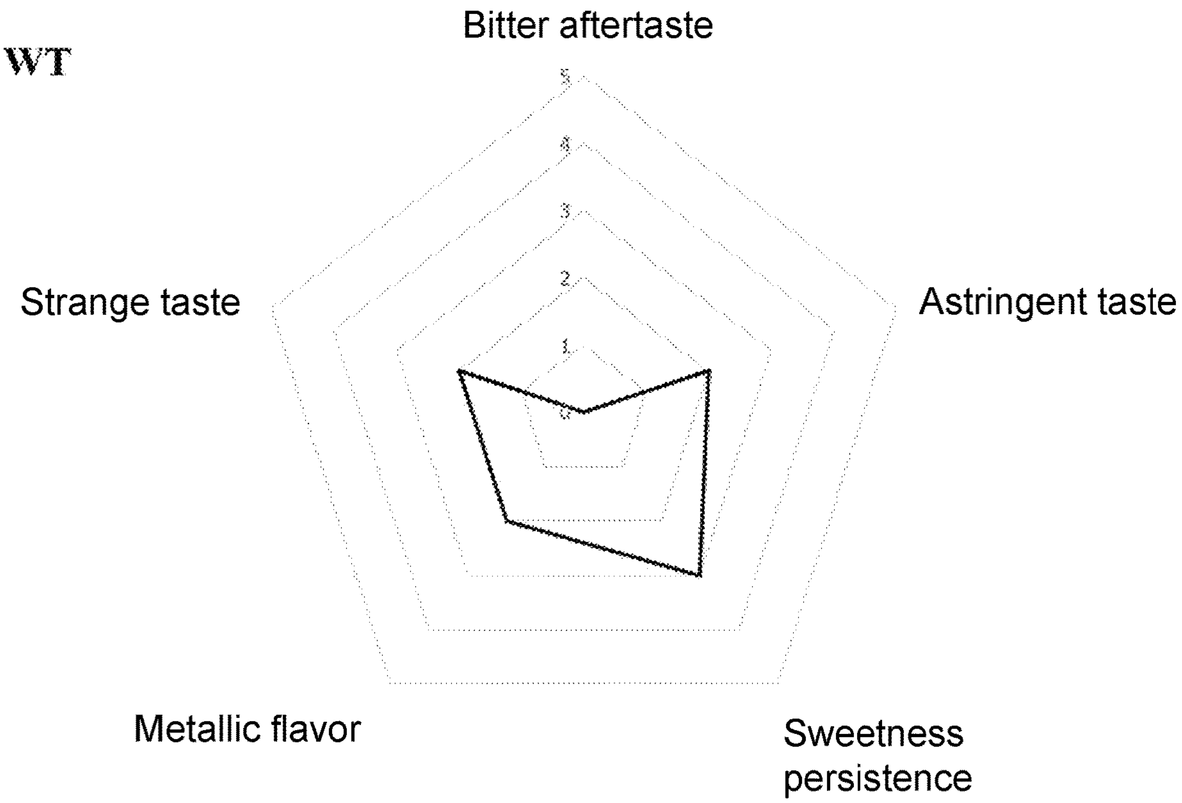
FIG. 1 is a schematic diagram illustrating a result of an off-flavor assessment on an original brazzein protein sample according to some embodiments of the present disclosure.
Figure 2:
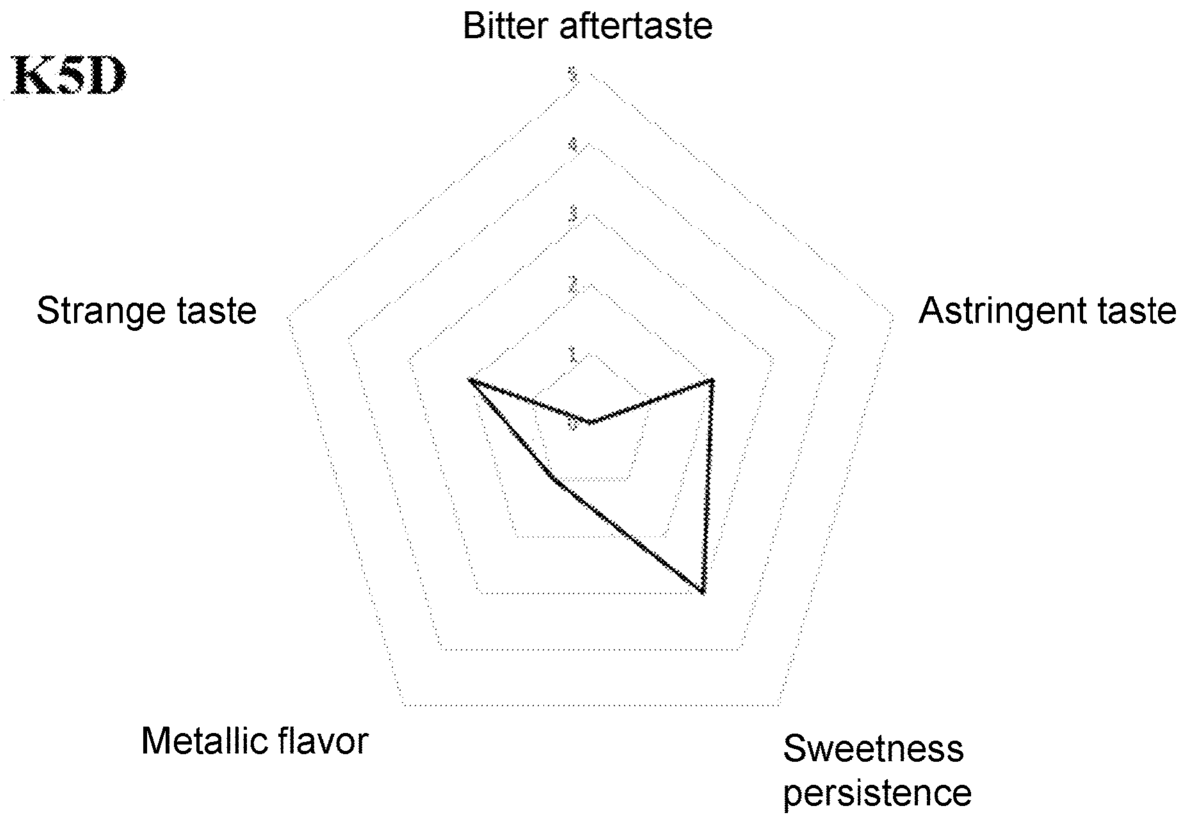
FIG. 2 is a schematic diagram illustrating a result of an off-flavor assessment on a brazzein mutant sample K5D according to some embodiments of the present disclosure.
Figure 3:
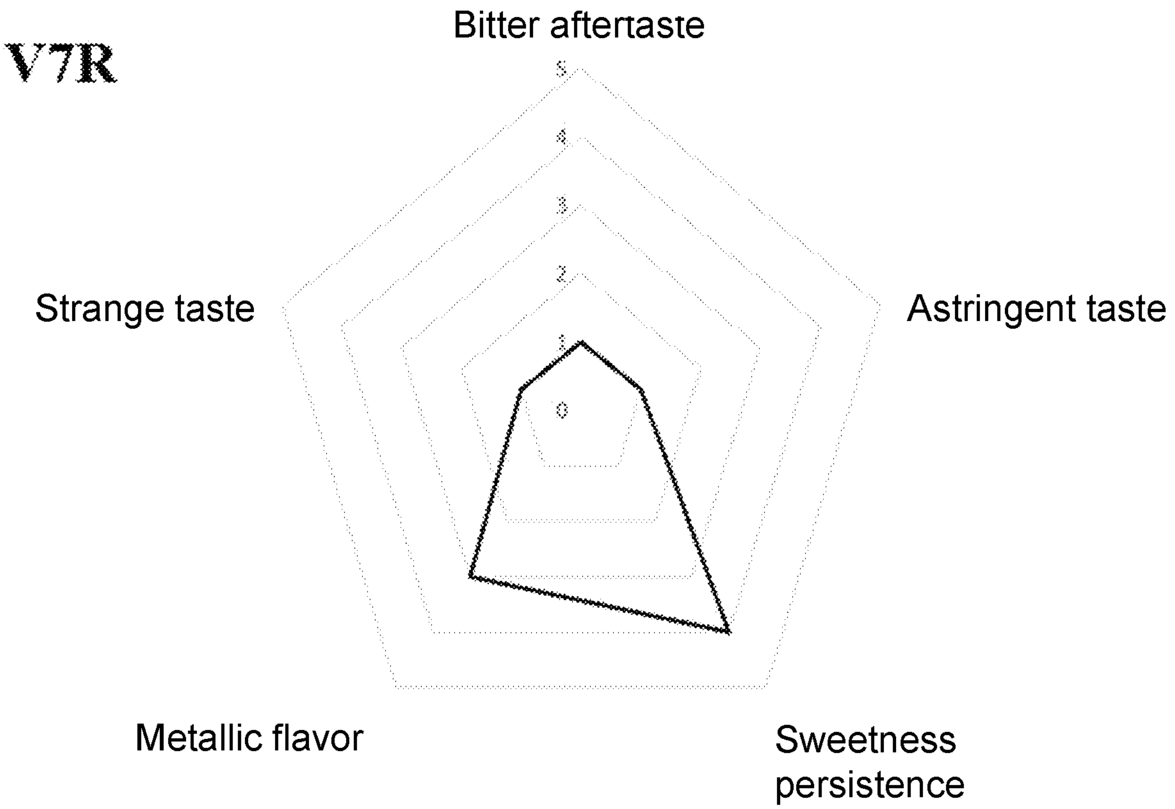
FIG. 3 is a schematic diagram illustrating a result of an off-flavor assessment on a brazzein mutant sample V7R according to some embodiments of the present disclosure.
Figure 4:
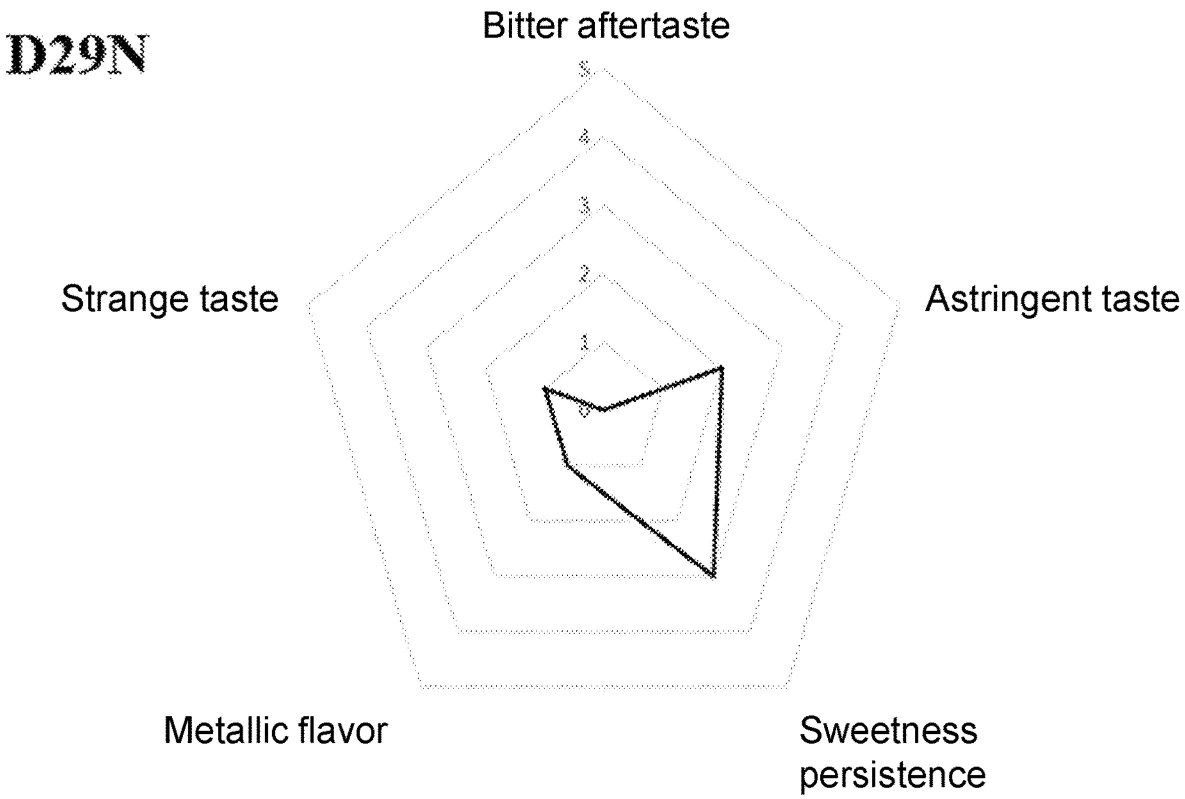
FIG. 4 is a schematic diagram illustrating a result of an off-flavor assessment on a brazzein mutant sample D29N according to some embodiments of the present disclosure.
Figure 5:
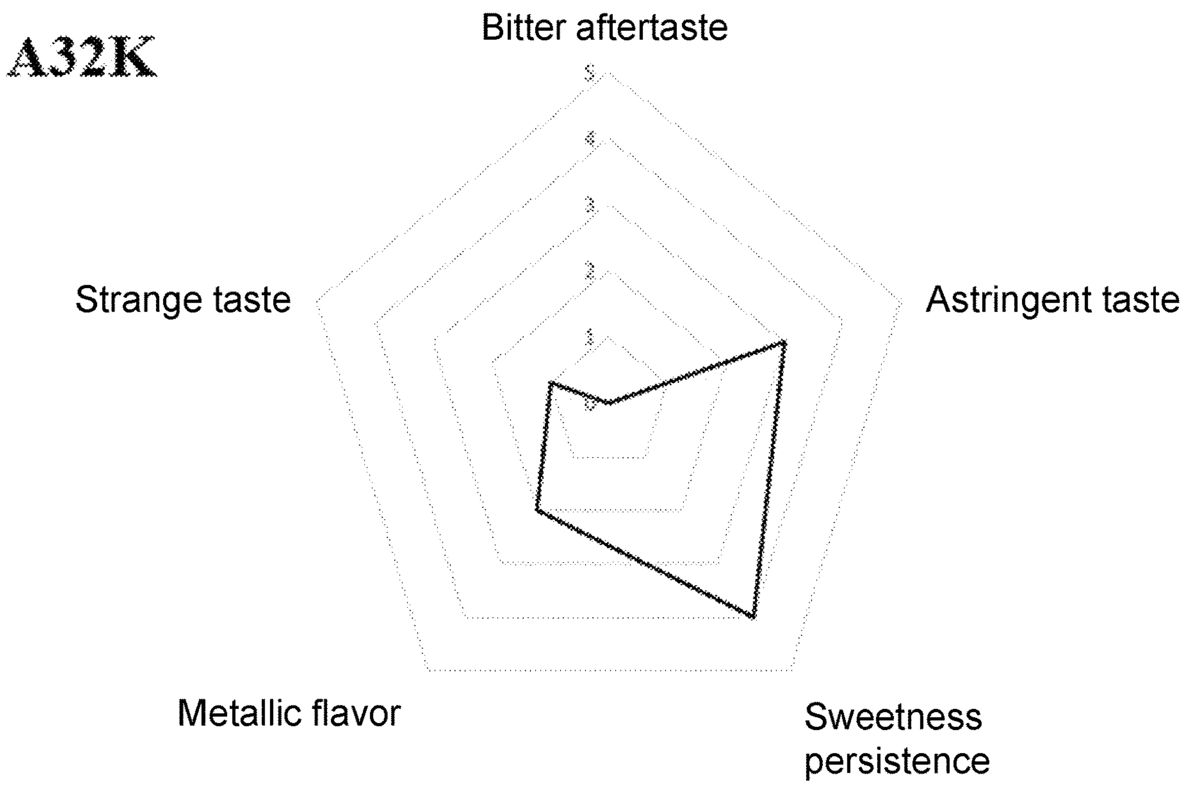
FIG. 5 is a schematic diagram illustrating a result of an off-flavor assessment on a brazzein mutant sample A32K according to some embodiments of the present disclosure.
Figure 6:
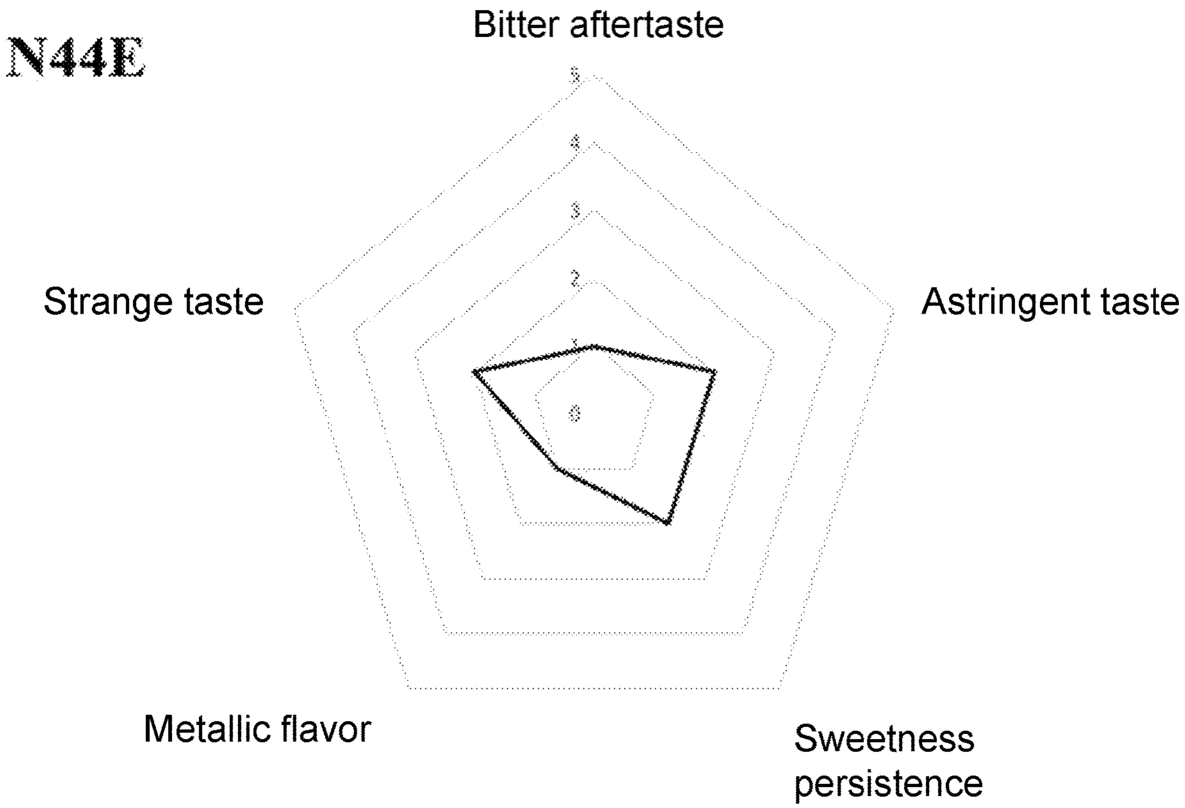
FIG. 6 is a schematic diagram illustrating a result of an off-flavor assessment on a brazzein mutant sample N44E according to some embodiments of the present disclosure.
Figure 7:
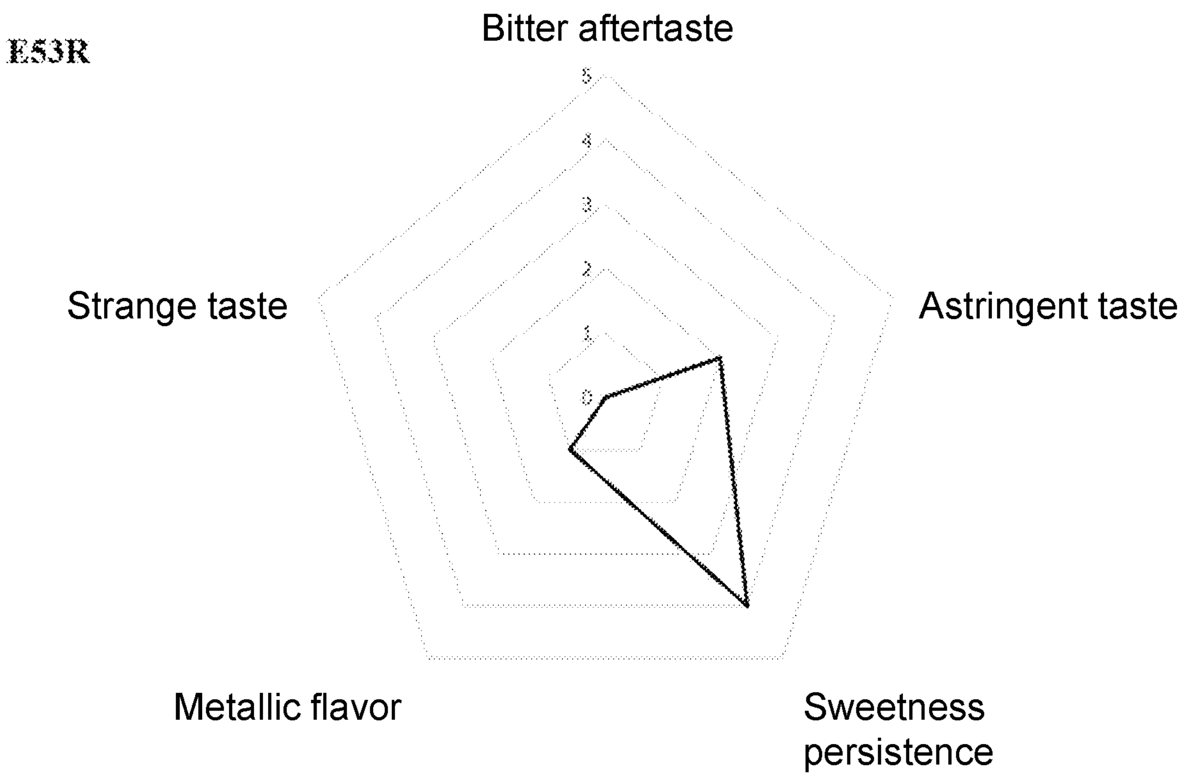
FIG. 7 is a schematic diagram illustrating a result of an off-flavor assessment on a brazzein mutant sample E53R according to some embodiments of the present disclosure.
Figure 8:
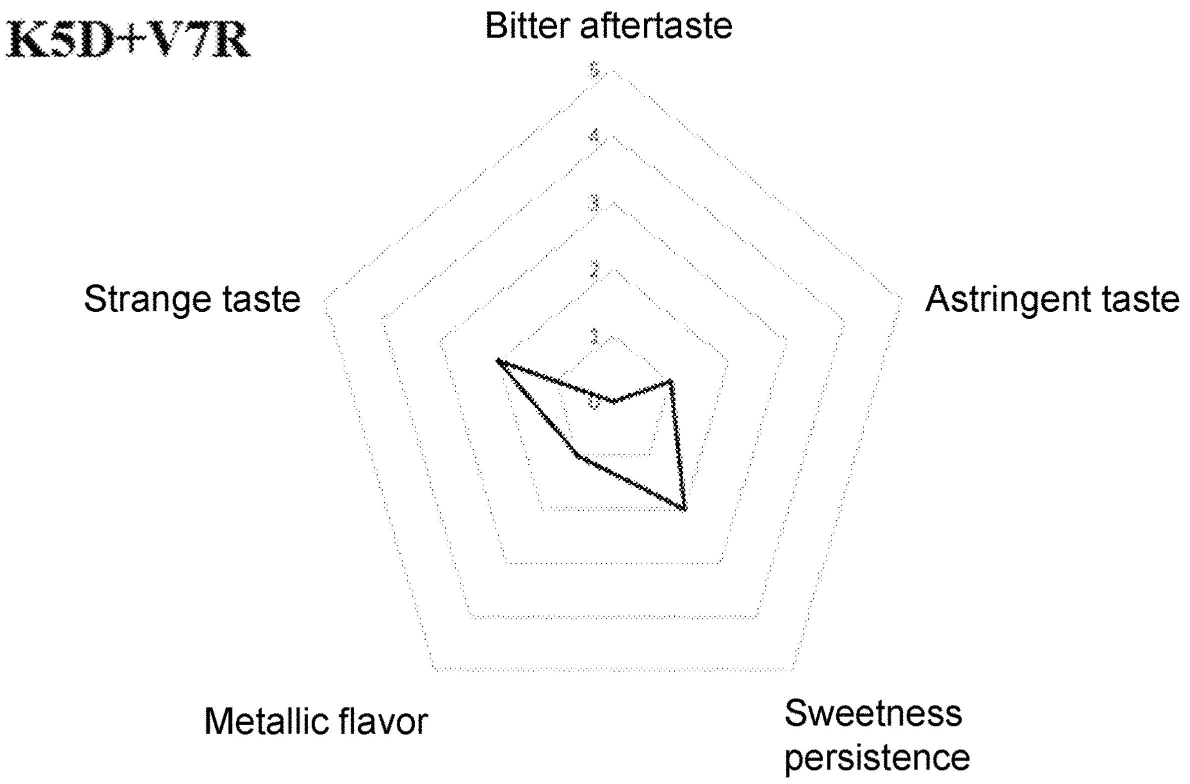
FIG. 8 is a schematic diagram illustrating a result of an off-flavor assessment on a brazzein mutant sample K5D+V7R according to some embodiments of the present disclosure.
Figure 9:
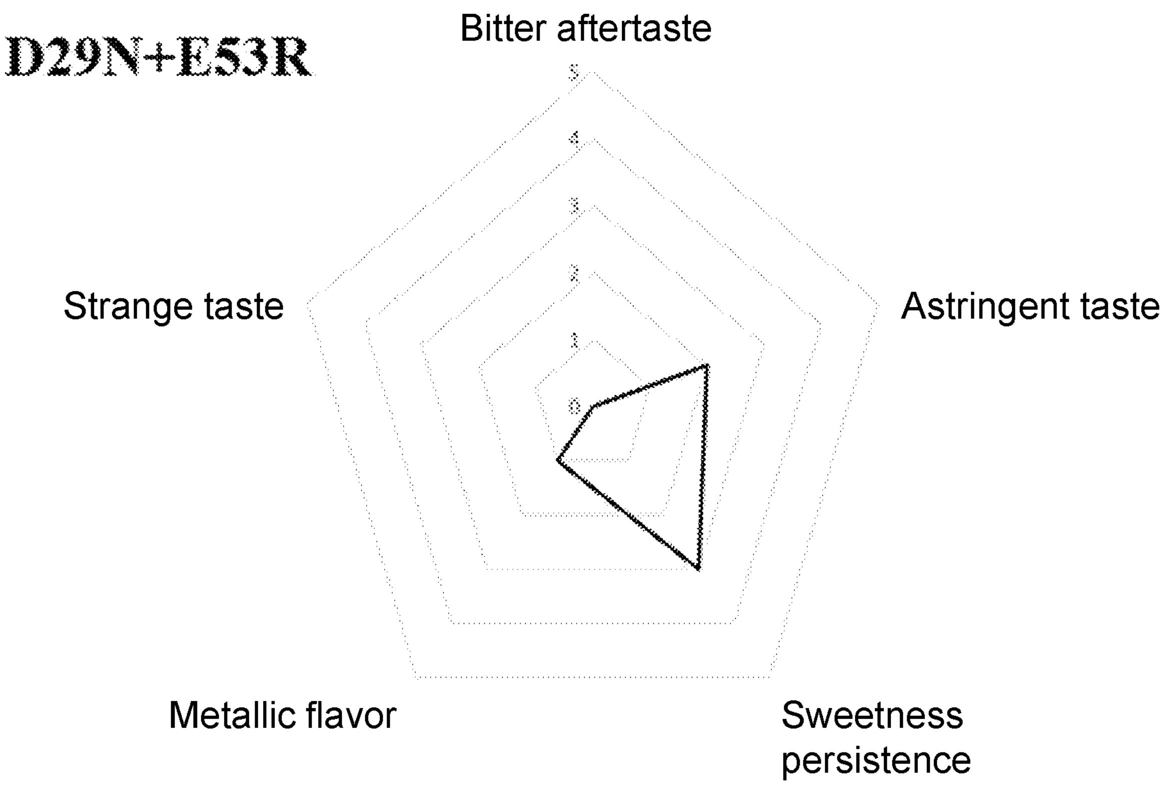
FIG. 9 is a schematic diagram illustrating a result of an off-flavor assessment on a brazzein mutant sample D29N+E53R according to some embodiments of the present disclosure.
Figure 10:
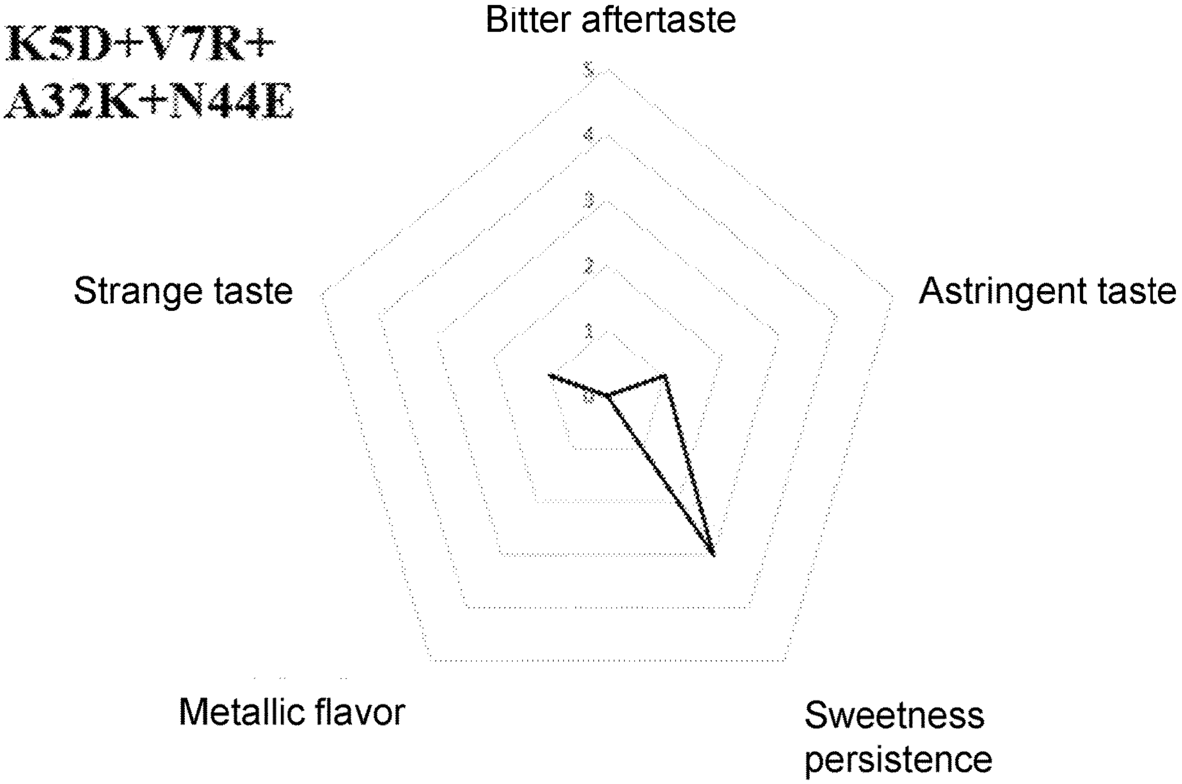
FIG. 10 is a schematic diagram illustrating a result of an off-flavor assessment on a brazzein mutant sample K5D+V7R+A32K+N44E according to some embodiments of the present disclosure.
Figure 11:
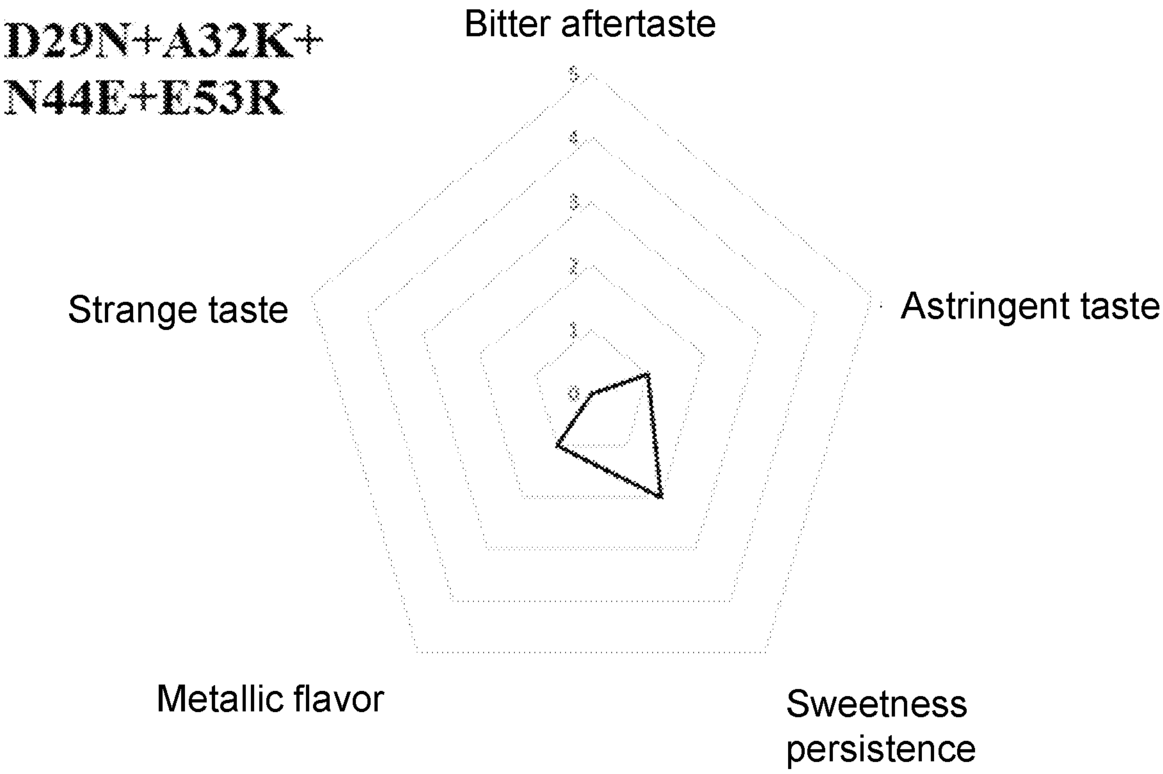
FIG. 11 is a schematic diagram illustrating a result of an off-flavor assessment on a brazzein mutant sample D29N+A32K+N44E+E53R according to some embodiments of the present disclosure.
Figure 12:
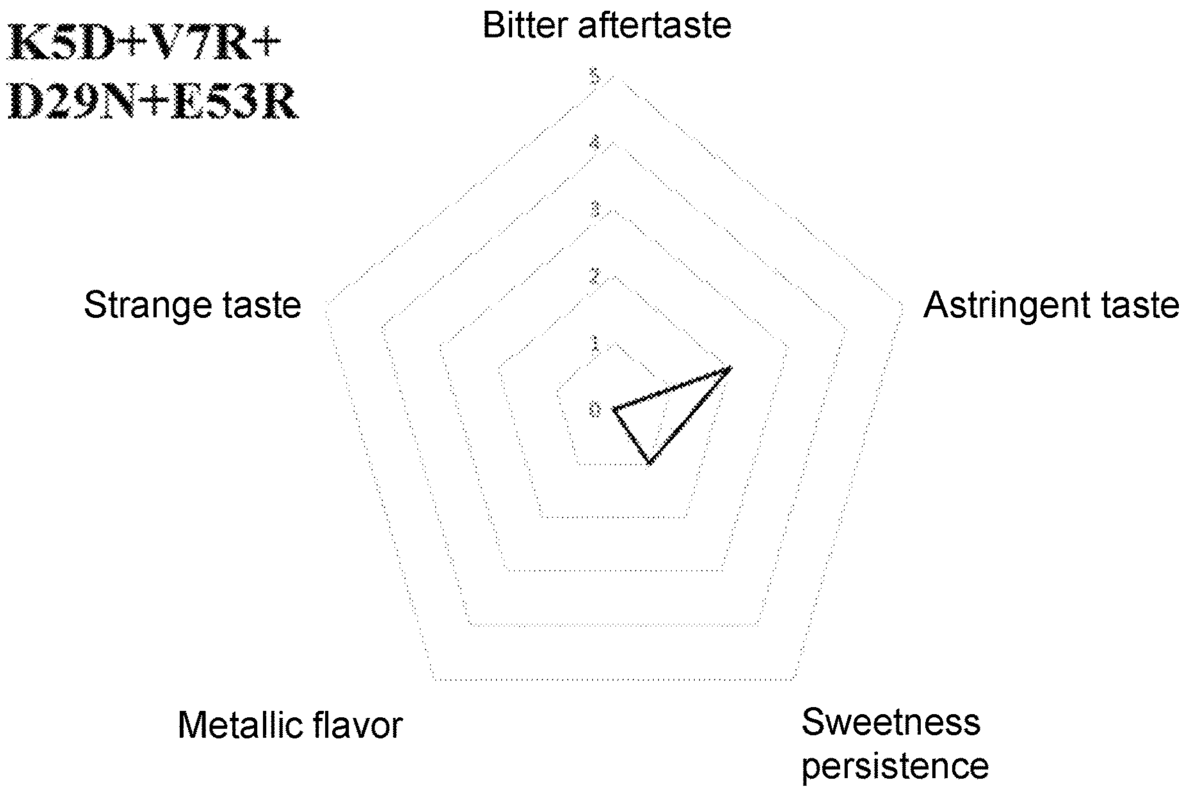
FIG. 12 is a schematic diagram illustrating a result of an off-flavor assessment on a brazzein mutant sample K5D+V7R+D29N+E53R according to some embodiments of the present disclosure.
Figure 13:
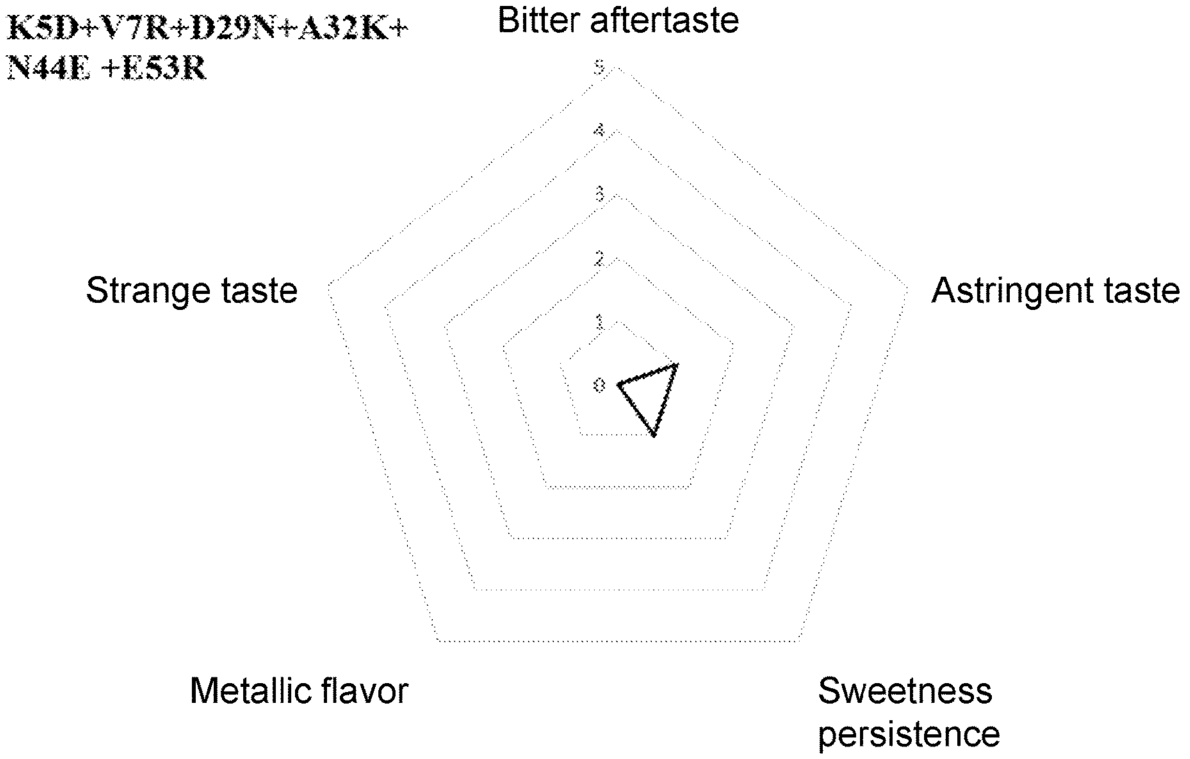
FIG. 13 is a schematic diagram illustrating a result of an off-flavor assessment on a brazzein mutant sample K5D+V7R+D29N+A32K+N44E+E53R according to some embodiments of the present disclosure.

In order to more clearly illustrate the technical solutions of the embodiments of the present disclosure, a brief introduction to the embodiments is given below.

As shown in the present disclosure and in the claims, unless the context clearly suggests an exception, the words "one," "a," "an," "one kind," and/or "the" do not refer specifically to the singular, but may also include the plural. Generally, the terms "including" and "comprising" suggest only the inclusion of clearly identified steps and elements, however, the steps and elements that do not constitute an exclusive list, and the method or apparatus may also include other steps or elements.

Currently, in the pursuit of higher sweetness of sweet proteins, it is prone to introducing severe taste defects (e.g., significant sweet taste lag time and severe off-flavors), which gives rise to the technical challenge that "the higher the sweetness, the poorer the taste". Previously, enhancing the sweetness of sweet proteins has always been the primary objective. Higher sweetness indicates a tighter binding of the sweetener to the receptor protein, yet this also often results in the palatability of the sweet taste being inferior to that of traditional sucrose.

In order to overcome this technical challenge, the present disclosure provides sweet protein mutants, preparation methods, and use thereof. According to the present disclosure, the sweet protein gene is artificially and targeted modified using genetic engineering techniques.

The embodiments of the present disclosure provide a sweet protein mutant derived from a sweet protein having an amino acid sequence set forth in SEQ ID NO. 1, the mutation including amino acid mutations relative to SEQ ID NO: 1 selected from at least one of K5D, V7R, D29N, A32K, N44E, or E53R. The K5D amino acid mutation is a mutation of lysine (K) at position 5 of the amino acid sequence to aspartic acid (D), the V7R amino acid mutation is a mutation of valine (V) at position 7 of the amino acid sequence to arginine (R), the D29N amino acid mutation is a mutation of aspartic acid (D) at position 29 of the amino acid sequence to asparagine (N), the A32K amino acid mutation is a mutation of alanine (A) at position 32 of the amino acid sequence to lysine (K), the N44E amino acid mutation is a mutation of asparagine (N) at position 44 of the amino acid sequence to glutamic acid (E), and the E53R amino acid mutation is a mutation of glutamic acid (E) at position 53 of the amino acid sequence to arginine (R).

According to the embodiments of the present disclosure, the sweet protein mutant is obtained by introducing at least one amino acid mutation selected from K5D, V7R, D29N, A32K, N44E, and E53R in the sweet protein with the amino acid sequence set forth in SEQ ID NO. 1. Compared with sweet protein corresponding to an original amino acid sequence, the synergistic optimization of sweetness and taste is achieved, which pioneers a new technical direction for the development of sweet proteins.

In some embodiments, the one or more amino acid mutations are at least one of K5D, V7R, D29N, A32K, N44E, E53R, K5D+V7R (same as "K5D and V7R", "+" indicates mutations in the same sequence), D29N+E53R, K5D+V7R+A32K+N44E, D29N+A32K+N44E+E53R, K5D+V7R+D29N+E53R, or K5D+V7R+D29N+A32K+N44E+E53R. In some embodiments, the one or more amino acid mutations are at least one of E53R, D29N+E53R, or K5D+V7R+D29N+E53R. In some embodiments, the amino acid mutations are K5D+V7R+A32K+N44E. In some embodiments, the amino acid mutations are D29N+A32K+N44E+E53R. In some embodiments, the amino acid mutations are K5D+V7R+D29N+A32K+N44E+E53R.

```
SEQ ID NO. 1:
QDKCKKVYENYPVSKCQLANQCNYDCKLDKHARSGECFYDEKRNLQCIC

DYCEY.
```

In some embodiments, an unmutated sweet protein (i.e., an original sweet protein) is encoded by a nucleic acid sequence as set forth in SEQ ID NO. 2.

```
SEQ ID NO. 2:
CAGGACAAGTGCAAGAAGGTCTACGAGAACTACCCAGTTTCCAAGTGCC

AGTTGGCTAACCAGTGTAACTACGACTGCAAGTTGGACAAGCACGCTAG

ATCTGGTGAGTGTTTCTACGACGAGAAGAGAAACCTGCAGTGCATCTGT

GACTACTGCGAGTACTAA.
```

In some embodiments, an amino acid sequence of the sweet protein with a K5D mutant is set forth in SEQ ID NO. 11, and a nucleic acid sequence encoding the sweet protein with the K5D mutant is set forth in SEQ ID NO. 12.

```
SEQ ID NO. 11:
QDKCDKVYENYPVSKCQLANQCNYDCKLDKHARSGECFYDEKRNLQCIC

DYCEY.

SEQ ID NO. 12:
CAGGACAAGTGCGACAAGGTCTACGAGAACTACCCAGTTTCCAAGTGCC

AGTTGGCTAACCAGTGTAACTACGACTGCAAGTTGGACAAGCACGCTAG
```

-continued

ATCTGGTGAGTGTTTCTACGACGAGAAGAGAAACCTGCAGTGCATCTGT

GACTACTGCGAGTACTAA.

In some embodiments, an amino acid sequence of the sweet protein with a V7R mutant is set forth in SEQ ID NO. 13, and a nucleic acid sequence encoding the sweet protein with the V7R mutant is set forth in SEQ ID NO. 14.

SEQ ID NO. 13:
QDKCKKRYENYPVSKCQLANQCNYDCKLDKHARSGECFYDEKRNLQCIC

DYCEY.

SEQ ID NO. 14:
CAGGACAAGTGCAAGAAGCGCTACGAGAACTACCCAGTTTCCAAGTGCC

AGTTGGCTAACCAGTGTAACTACGACTGCAAGTTGGACAAGCACGCTAG

ATCTGGTGAGTGTTTCTACGACGAGAAGAGAAACCTGCAGTGCATCTGT

GACTACTGCGAGTACTAA.

In some embodiments, an amino acid sequence of the sweet protein with a D29N mutant is set forth in SEQ ID NO. 15, and a nucleic acid sequence encoding the sweet protein with the D29N mutant is set forth in SEQ ID NO. 16.

SEQ ID NO. 15:
QDKCKKVYENYPVSKCQLANQCNYDCKLNKHARSGECFYDEKRNLQCIC

DYCEY.

SEQ ID NO. 16:
CAGGACAAGTGCAAGAAGGTCTACGAGAACTACCCAGTTTCCAAGTGCC

AGTTGGCTAACCAGTGTAACTACGACTGCAAGTTGAACAAGCACGCTAG

ATCTGGTGAGTGTTTCTACGACGAGAAGAGAAACCTGCAGTGCATCTGT

GACTACTGCGAGTACTAA.

In some embodiments, an amino acid sequence of the sweet protein with an E53R mutant is set forth in SEQ ID NO. 17, and a nucleic acid sequence encoding the sweet protein with the E53R mutant is set forth in SEQ ID NO. 18.

SEQ ID NO. 17:
QDKCKKVYENYPVSKCQLANQCNYDCKLDKHARSGECFYDEKRNLQCIC

DYCRY.

SEQ ID NO. 18:
CAGGACAAGTGCAAGAAGGTCTACGAGAACTACCCAGTTTCCAAGTGCC

AGTTGGCTAACCAGTGTAACTACGACTGCAAGTTGGACAAGCACGCTAG

ATCTGGTGAGTGTTTCTACGACGAGAAGAGAAACCTGCAGTGCATCTGT

GACTACTGCAGATACTAA.

In some embodiments, an amino acid sequence of the sweet protein with a K5D+V7R mutant is set forth in SEQ ID NO. 19, and a nucleic acid sequence encoding the sweet protein with the K5D+V7R mutant is set forth in SEQ ID NO. 20.

SEQ ID NO. 19:
QDKCDKRYENYPVSKCQLANQCNYDCKLDKHARSGECFYDEKRNLQCIC

DYCEY.

SEQ ID NO. 20:
CAGGACAAGTGCGACAAGCGCTACGAGAACTACCCAGTTTCCAAGTGCC

AGTTGGCTAACCAGTGTAACTACGACTGCAAGTTGGACAAGCACGCTAG

ATCTGGTGAGTGTTTCTACGACGAGAAGAGAAACCTGCAGTGCATCTGT

GACTACTGCGAGTACTAA.

In some embodiments, an amino acid sequence of the sweet protein with a D29N+E53R mutant is set forth in SEQ ID NO. 21, and a nucleic acid sequence encoding the sweet protein with the D29N+E53R mutant is set forth in SEQ ID NO. 22.

SEQ ID NO. 21:
QDKCKKVYENYPVSKCQLANQCNYDCKLNKHARSGECFYDEKRNLQCIC

DYCRY.

SEQ ID NO. 22:
CAGGACAAGTGCAAGAAGGTCTACGAGAACTACCCAGTTTCCAAGTGCC

AGTTGGCTAACCAGTGTAACTACGACTGCAAGTTGAACAAGCACGCTAG

ATCTGGTGAGTGTTTCTACGACGAGAAGAGAAACCTGCAGTGCATCTGT

GACTACTGCAGATACTAA.

In some embodiments, an amino acid sequence of the sweet protein with a K5D+V7R+D29N+E53R mutant is set forth in SEQ ID NO. 23, and a nucleic acid sequence encoding the sweet protein with the K5D+V7R+D29N+E53R mutant is set forth in SEQ ID NO. 24.

SEQ ID NO. 23:
QDKCDKRYENYPVSKCQLANQCNYDCKLNKHARSGECFYDEKRNLQCIC

DYCRY.

SEQ ID NO. 24:
CAGGACAAGTGCGACAAGCGCTACGAGAACTACCCAGTTTCCAAGTGCC

AGTTGGCTAACCAGTGTAACTACGACTGCAAGTTGAACAAGCACGCTAG

ATCTGGTGAGTGTTTCTACGACGAGAAGAGAAACCTGCAGTGCATCTGT

GACTACTGCAGATACTAA.

In some embodiments, an amino acid sequence of the sweet protein with an A32K mutant is set forth in SEQ ID NO. 25, and a nucleic acid sequence encoding the sweet protein with the A32K mutant is set forth in SEQ ID NO. 26.

SEQ ID NO. 25:
QDKCKKVYENYPVSKCQLANQCNYDCKLDKHKRSGECFYDEKRNLQCIC

DYCEY.

SEQ ID NO. 26:
CAGGACAAGTGCAAGAAGGTCTACGAGAACTACCCAGTTTCCAAGTGCC

AGTTGGCTAACCAGTGTAACTACGACTGCAAGTTGGACAAGCACAAGAG

ATCTGGTGAGTGTTTCTACGACGAGAAGAGAAACCTGCAGTGCATCTGT

GACTACTGCGAGTACTAA

In some embodiments, an amino acid sequence of the sweet protein with a N44E mutant is set forth in SEQ ID NO.

27, and a nucleic acid sequence encoding the sweet protein with the N44E mutant is set forth in SEQ ID NO. 28.

```
SEQ ID NO. 27:
QDKCKKVYENYPVSKCQLANQCNYDCKLDKHARSGECFYDEKRELQCIC

DYCEY.

SEQ ID NO. 28:
CAGGACAAGTGCAAGAAGGTCTACGAGAACTACCCAGTTTCCAAGTGCC

AGTTGGCTAACCAGTGTAACTACGACTGCAAGTTGGACAAGCACGCTAG

ATCTGGTGAGTGTTTCTACGACGAGAAGAGAGAGCTGCAGTGCATCTGT

GACTACTGCGAGTACTAA.
```

In some embodiments, an amino acid sequence of the sweet protein with a K5D+V7R+A32K+N44E mutant is set forth in SEQ ID NO. 29, and a nucleic acid sequence encoding the sweet protein with the K5D+V7R+A32K+N44E mutant is set forth in SEQ ID NO. 30.

```
SEQ ID NO. 29:
QDKCDKRYENYPVSKCQLANQCNYDCKLDKHKRSGECFYDEKRELQCIC

DYCEY.

SEQ ID NO. 30:
CAGGACAAGTGCGACAAGCGCTACGAGAACTACCCAGTTTCCAAGTGCC

AGTTGGCTAACCAGTGTAACTACGACTGCAAGTTGGACAAGCACAAGAG

ATCTGGTGAGTGTTTCTACGACGAGAAGAGAGAGCTGCAGTGCATCTGT

GACTACTGCGAGTACTAA
```

In some embodiments, an amino acid sequence of the sweet protein with a D29N+A32K+N44E+E53R mutant is set forth in SEQ ID NO. 31, and a nucleic acid sequence encoding the sweet protein with the D29N+A32K+N44E+E53R mutant is set forth in SEQ ID NO. 32.

```
SEQ ID NO. 31:
QDKCKKVYENYPVSKCQLANQCNYDCKLNKHKRSGECFYDEKRELQCIC

DYCRY.

SEQ ID NO. 32:
CAGGACAAGTGCAAGAAGGTCTACGAGAACTACCCAGTTTCCAAGTGCC

AGTTGGCTAACCAGTGTAACTACGACTGCAAGTTGAACAAGCACAAGAG

ATCTGGTGAGTGTTTCTACGACGAGAAGAGAGAGCTGCAGTGCATCTGT

GACTACTGCAGATACTAA
```

In some embodiments, an amino acid sequence of the sweet protein with a K5D+V7R+D29N+A32K+N44E+E53R mutant is set forth in SEQ ID NO. 33, and a nucleic acid sequence encoding the sweet protein with the K5D+V7R+D29N+A32K+N44E+E53R mutant is set forth in SEQ ID NO. 34.

```
SEQ ID NO. 33:
QDKCDKRYENYPVSKCQLANQCNYDCKLNKHKRSGECFYDEKRELQCIC

DYCRY.

SEQ ID NO. 34:
CAGGACAAGTGCGACAAGCGCTACGAGAACTACCCAGTTTCCAAGTGCC

AGTTGGCTAACCAGTGTAACTACGACTGCAAGTTGAACAAGCACAAGAG
```

-continued

```
ATCTGGTGAGTGTTTCTACGACGAGAAGAGAGAGCTGCAGTGCATCTGT

GACTACTGCAGATACTAA
```

In some embodiments, the unmutated sweet protein is derived from the West African tropical plant *Pentadiplandra brazzeana* Baillon.

In some embodiments, an off-flavor of the sweet protein mutant is less than an off-flavor of the sweet protein. The off-flavor may include at least one of astringency, metallic taste, bitterness, or astringent aftertaste.

In some embodiments, the sweet protein mutant exhibits a reduced sweet taste lag time and a reduced sweet taste residual time compared to the sweet protein. Sweet taste lag time refers to the period from the initial contact between a sweet substance and oral taste receptors to the moment when a taster first clearly and stably perceives the sweet taste. Sweet taste residual time refers to the duration from the moment a taster first perceives the sweet taste until the sweet taste in the mouth completely fades away without any sweet aftertaste.

The embodiments of the present disclosure provide a nucleic acid molecule encoding a sweet protein mutant.

The embodiments of the present disclosure provide an expression vector comprising at least one copy of a nucleic acid molecule.

The embodiments of the present disclosure provide a sweet protein mutant transformant. The sweet protein mutant transformant is a genetically engineered strain that expresses a sweet protein mutant.

The embodiments of the present disclosure provide a preparation method for a sweet protein mutant. The preparation method comprises constructing an expression vector, the expression vector comprising at least one copy of a nucleic acid sequence that encodes the sweet protein mutant; constructing a sweet protein mutant transformant by transforming the expression vector into a recipient cell; and obtaining the sweet protein mutant by culturing the sweet protein mutant transformant and collecting a culture.

In some embodiments, the preparation method for the sweet protein mutant further comprises: synthesizing a nucleic acid fragment encoding a sweet protein derived from a West African tropical plant *Pentadiplandra brazzeana* Baillon via whole gene synthesis, the nucleic acid fragment having a sequence as set forth in SEQ ID NO. 2, and ligating the nucleic acid fragment into an expression vector via restriction enzyme digestion to obtain a recombinant plasmid; performing site-directed mutagenesis using the recombinant plasmid as a template to obtain the expression vector comprising at least one copy of the nucleic acid sequence of the sweet protein mutant; and transforming the expression vector comprising at least one copy of the nucleic acid sequence of the sweet protein mutant into a host cell for culturing to obtain the sweet protein mutant.

In some embodiments, the host cell is *Pichia pastoris* X-33.

The embodiments of the present disclosure provide a purification method for a sweet protein mutant. The purification method comprises: culturing a sweet protein mutant transformant to collect a culture, separating and removing contaminating proteins from the culture and filtering, adsorbing the sweet protein mutant from a filtered solution through a cation exchange resin, followed by eluting to collect an eluent, performing nanofiltration on the eluent for desalination and concentration, and performing lyophilization on a nanofiltered eluent to obtain a purified sweet protein mutant, the sweet protein mutant transformant comprising a nucleic acid molecule encoding the sweet protein mutant.

In some embodiments, the contaminating proteins are separated and removed from the culture via centrifugal separation.

In some embodiments, the filtering is performed using a 0.5-10 kDa ultrafiltration membrane. In some embodiments, the filtering is performed using a 0.5 kDa ultrafiltration membrane, a 1 kDa ultrafiltration membrane, a 2 kDa ultrafiltration membrane, a 3 kDa ultrafiltration membrane, a 4 kDa ultrafiltration membrane, a 5 kDa ultrafiltration membrane, a 6 kDa ultrafiltration membrane, a 7 kDa ultrafiltration membrane, an 8 kDa ultrafiltration membrane, a 9 kDa ultrafiltration membrane, or a 10 kDa ultrafiltration membrane.

In some embodiments, the eluting is performed using a NaCl aqueous solution.

In some embodiments, in the NaCl aqueous solution, a NaCl concentration is within a range of 1-2 M. In some embodiments, the NaCl concentration in the NaCl aqueous solution is 1 M, 1.3 M, 1.5 M, 1.8 M, or 2 M. In some embodiments, a pH of the NaCl aqueous solution is within a range of 3.0-7.0. In some embodiments, the pH of the NaCl aqueous solution is 3.0, 3.5, 4.0, 4.5, 5.0, 5.5, 6.0, 6.5, or 7.0.

In some embodiments of the present disclosure, the sweet protein mutant is obtained by performing site-directed mutagenesis on the amino acid sequence of the sweet protein. Compared with the original sweet protein, the sweetness of the sweet protein mutant is significantly improved, and the sweetness of the sweet protein mutant is 1.6-6 times that of the original sweet protein.

The technical solution of the present disclosure will be further described in detail with reference to the specific examples. It should be understood that the following examples are only intended to exemplify and explain the present disclosure and should not be construed as limiting the scope of protection of the present disclosure. All technologies implemented based on the above contents of the present disclosure are included in the scope of protection intended by the present disclosure.

EXAMPLES

Example 1: Construction of Brazzein Recombinant Plasmid

Sangon Biotech (Shanghai) Co., Ltd. synthesized a nucleic acid fragment encoding a brazzein protein derived from a West African tropical plant *Pentadiplandra brazzeana* Baillon via whole gene synthesis, the nucleic acid fragment having a sequence as set forth in SEQ ID NO. 2, and ligated the nucleic acid fragment into an expression vector pPICZαA via a DNA ligase after digestion with restriction enzymes XhoI and NotI (purchased from New England Biolabs and operated according to the instructions) to obtain a recombinant plasmid Brazzein-pPICZαA.

Example 2: Construction of Brazzein Mutant

The site-directed mutagenesis was performed using the recombinant plasmid Brazzein-pPICZαA as a template using forward/reverse mutation primers of K5D, V7R, D29N, A32K, N44E, and E53R, respectively via the Fast Mutagenesis System of the TransGen Biotech to obtain the brazzein mutant.

Where lysine (K) at position 5 of the amino acid sequence was mutated to aspartic acid (D), a nucleic acid sequence of the forward mutation primer K5D-F was as set forth in SEQ ID NO. 3:

```
5' GAAAAGACAGGACAAGTGCGACAAGGTCTACGAGAACTAC 3';
```

a nucleic acid sequence of the reverse mutation primer K5D-R was as set forth in SEQ ID NO. 4:

```
5' GTAGTTCTCGTAGACCTTGTCGCACTTGTCCTGTCTTTTC 3';
```

valine (V) at position 7 of the amino acid sequence was mutated to arginine (R), a nucleic acid sequence of the forward mutation primer V7R-F was as set forth in SEQ ID NO. 5:

```
5' GACAAGTGCAAGAAGCGCTACGAGAACTACC 3';
```

a nucleic acid sequence of the reverse mutation primer V7R-R was as set forth in SEQ ID NO. 6:

```
5' GGTAGTTCTCGTAGCGCTTCTTGCACTTGTC 3';
```

aspartic acid (D) at position 29 of the amino acid sequence was mutated to asparagine (N), a nucleic acid sequence of the forward mutation primer D29N-F was as set forth in SEQ ID NO. 7:

```
5' CTACGACTGCAAGTTGAACAAGCACGCTAGATC 3';
```

a nucleic acid sequence of the reverse mutation primer D29N-R was as set forth in SEQ ID NO. 8:

```
5' GATCTAGCGTGCTTGTTCAACTTGCAGTCGTAG 3';
```

alanine (A) at position 32 of the amino acid sequence was mutated to lysine (K), a nucleic acid sequence of the forward mutation primer A32K-F was as set forth in SEQ ID NO. 35:

```
GCAAGTTGGACAAGCACAAGAGATCTGGTGAGTGTTTC;
```

a nucleic acid sequence of the reverse mutation primer A32K-R was as set forth in SEQ ID NO. 36:

```
GAAACACTCACCAGATCTCTTGTGCTTGTCCAACTTGC;
```

asparagine (N) at position 44 of the amino acid sequence was mutated to glutamic acid (E), a nucleic acid sequence of the forward mutation primer N44E-F was as set forth in SEQ ID NO. 37:

```
CTACGACGAGAAGAGAGAGCTGCAGTGCATCTGTG;
```

a nucleic acid sequence of the reverse mutation primer N44E-R was as set forth in SEQ ID NO. 38:

```
CACAGATGCACTGCAGCTCTCTCTTCTCGTCGTAG;
```

glutamic acid (E) at position 53 of the amino acid sequence was mutated to arginine (R), a nucleic acid sequence of the forward mutation primer E53R-F was as set forth in SEQ ID NO. 9:

```
5' ATCTGTGACTACTGCAGATACTAAGCG 3';
```

a nucleic acid sequence of the reverse mutation primer E53R-R was as set forth in SEQ ID NO. 10:

```
5' TCTGCAGTAGTCACAGATGCACTGCAG 3'.
```

A PCR system contained 25 μL of 2× TransStart® FastPfu Fly PCR SuperMix, 1 μL of 10 UM forward primer and 1 μL of 10 μM reverse primer, and 1 μL of 50 ng/μL template plasmid, $ddH_2O$ was supplemented to 50 μL. A PCR amplification process comprised: performing pre-denaturation at a temperature of 94 °C for 3 min followed by 30 cycles of: denaturation at the temperature of 94 °C for 20 s, annealing at the temperature of 55 °C for 20 s, extending at the temperature of 72 °C for 2 min; and finally extending at the temperature of 72 °C for 10 min. A PCR amplification product was digested with DpnI for 2 h, a digested product was transformed into *E. coli* Tran5α and preserved after monoclonal sequencing for verification.

Example 3: Expression of Brazzein Recombinant Plasmid and Brazzein Mutant in *Pichia pastoris*

The recombinant plasmid Brazzein-pPICZαA in Example 1 and the brazzein mutant in Example 2 were linearized with SacI, respectively. The linearized products were purified by a column purification kit, transformed into *Pichia pastoris* X-33 by electroporation, and spread on YPD+Zeocin (100 mg/L) plates. Strains grown on the YPD+Zeocin (100 mg/L) plates were engineered *Pichia pastoris* strains. Verification by shake-flask fermentation comprised: selecting transformants to be inoculated into a buffered glycerol-complex (BMGY) medium for shaking cultivation at 30 °C and 220 rpm for 24 h, then transferring to a buffered methanol-complex (BMMY) medium for shaking cultivation at 30 °C and 220 rpm, adding 0.5% methanol every 24 h to induce expression, and after 4 d, performing centrifugal separation to remove the strains and collecting a fermentation supernatant containing the brazzein protein.

Example 4: Purification of Brazzein Protein and Brazzein Mutant (a) Pretreatment of the Fermentation Supernatant 8000 g of the fermentation supernatant containing the brazzein protein obtained in Example 3 was centrifugally separated for 30 min to collect a supernatant solution.

(b) Crude Treatment of the Fermentation Supernatant

The supernatant solution after the pretreatment in step (a) was ultrafiltered using a 1 kDa ultrafiltration membrane for concentration and desalination. During the concentration, pure water was continuously added to dilute a salt concentration in a concentrated solution until its conductivity was less than 0.1 mS/m.

(c) Purification of the Brazzein Protein

Protein purification resin column: specification: 10×30 cm (1 L); filler: CM cation resin (6% cross-linked agarose, purchased from Suzhou Zhongke Senhui Microsphere Technology).

Equilibration: the resin column was equilibrated with 3 L acetic acid aqueous solution with a pH of 4.0 at a flow rate of 10 mL/min.

Sample loading: 5 L sample after the crude treatment in step (b) was loaded at a flow rate of 5 mL/min.

Washing: the sample was washed with the 3 L acetic acid aqueous solution with a pH of 4.0 at the flow rate of 10 mL/min.

Elution: the sample was eluted with 3 L 1 M acetic acid solution of NaCl at the flow rate of 10 mL/min to obtain an eluate containing the brazzein protein.

(d) Concentration and Desalination of the Eluate

The eluate obtained in step (c) was filtered through a nanofiltration membrane (1000 Da, Shanghai Langji Membrane Separation Equipment Engineering Co., Ltd.) for desalination to obtain a concentrated sample.

(e) Lyophilization of the Concentrated Sample

Excess water of the concentrated sample obtained in step (d) was removed using a lyophilizer to obtain a dried brazzein protein sample.

Example 5: Sensory Evaluation of Brazzein Protein and Brazzein Mutant

The sweetness of the sweet protein was verified using a blind test. A control group of the blind test used a 2% sucrose aqueous solution. The sweet protein samples to be tested were prepared into different concentration gradients of solutions and these solutions were randomly numbered. An evaluation team consisting of ten persons tasted the solutions and determined a solution with the same or similar sweetness as the 2% sucrose aqueous solution in the different concentration gradients of solutions, so as to calculate the relative sweetness of the samples.

Firstly, 1.0 g sweet protein sample was weighed and diluted to 100 mL with distilled water, i.e., a sample solution with a concentration of 1.0% was prepared; then 1.0% sample solution was taken and further diluted with the distilled water to form test solutions with different dilution multiples, whose concentration was 0.5%, 0.25%, 0.2%, 0.125%, 0.1%, 0.05%, 0.025%, and 0.0125%, respectively. The sweet protein samples to be tested were prepared into different concentration gradients of solutions and these solutions were randomly numbered. An evaluation team consisting of ten persons tasted the solutions and determined a solution with the same or similar sweetness as the 2% sucrose aqueous solution in the different concentration gradients of solutions, so as to calculate the relative sweetness of the samples. The formula is expressed as: the relative sweetness=2% sucrose aqueous solution/(1.0% sample solution×dilution multiple).

The test results are shown in Table 1.

TABLE 1

| Sweet protein | Relative sweetness (multiple relative to the sweetness of 2% sucrose aqueous solution) |
|---|---|
| WT (Original brazzein protein) | 500 |
| K5D | 800 |
| V7R | 1200 |
| D29N | 1500 |
| A32K | 700 |
| N44E | 600 |
| E53R | 1000 |
| K5D + V7R | 1500 |
| D29N + E53R | 2000 |
| K5D + V7R + A32K + N44E | 2000 |
| D29N + A32K + N44E + E53R | 2500 |

TABLE 1-continued

| Sweet protein | Relative sweetness (multiple relative to the sweetness of 2% sucrose aqueous solution) |
|---|---|
| K5D + V7R + D29N + E53R | 3000 |
| K5D + V7R + D29N + A32K + N44E + E53R | 5000 |

As can be seen from the above that the sweetness of the brazzein mutant of the present disclosure is 1.2-10 times that of the original brazzein protein (WT). In particular, the brazzein mutant K5D+V7R+D29N+A32K+N44E+E53R has achieved an unexpectedly remarkable enhancement in sweetness compared with the other brazzein mutants and the original brazzein protein.

Example 6: Off-Flavor Evaluation

The evaluation panel conducted an off-flavor assessment on samples including brazzein mutants (K5D, V7R, D29N, A32K, N44E, E53R, K5D+V7R, D29N+E53R, K5D+V7R+A32K+N44E, D29N+A32K+N44E+E53R, K5D+V7R+D29N+E53R, K5D+V7R+D29N+A32K+N44E+E53R), the original brazzein protein (WT), and a blank control (2% sucrose solution), all of which were adjusted to an equivalent sweetness level. The panelists performed intensity scoring on a 0-5 point scale for off-flavor of the samples including bitter aftertaste, metallic flavor, astringent taste, and sweetness persistence (0=no off-flavor, 5=extremely strong off-flavor). The results are shown in FIGS. 1 to 13. The WT protein exhibited a distinct astringent taste and a moderate intensity score (3 points) for sweetness persistence; its overly prolonged sweet taste persistence led to an unclean aftertaste, with the scores for all the above off-flavor exceeding 1 point.

The brazzein mutants of the present disclosure effectively reduced the intensities of astringent taste, bitter aftertaste, and sweetness persistence, resulting in a fresher taste profile, and their overall taste acceptability was superior to that of the original brazzein protein (WT). In particular, the brazzein mutant K5D+V7R+D29N+A32K+N44E+E53R not only showed a higher sweetness level compared with other brazzein mutants but also achieved the optimal performance in the off-flavor evaluation. This demonstrates that the brazzein mutants of the present disclosure, while improving the sweetness, have successfully suppressed the inherent undesirable off-flavors of the original brazzein protein (WT), overcome the taste defects of the original brazzein protein (WT), and thus possess a purer and more pleasant flavor characteristic.

Example 7: Evaluation of Sweet Taste Perception Kinetics (Time-Intensity Method)

Figure 14:
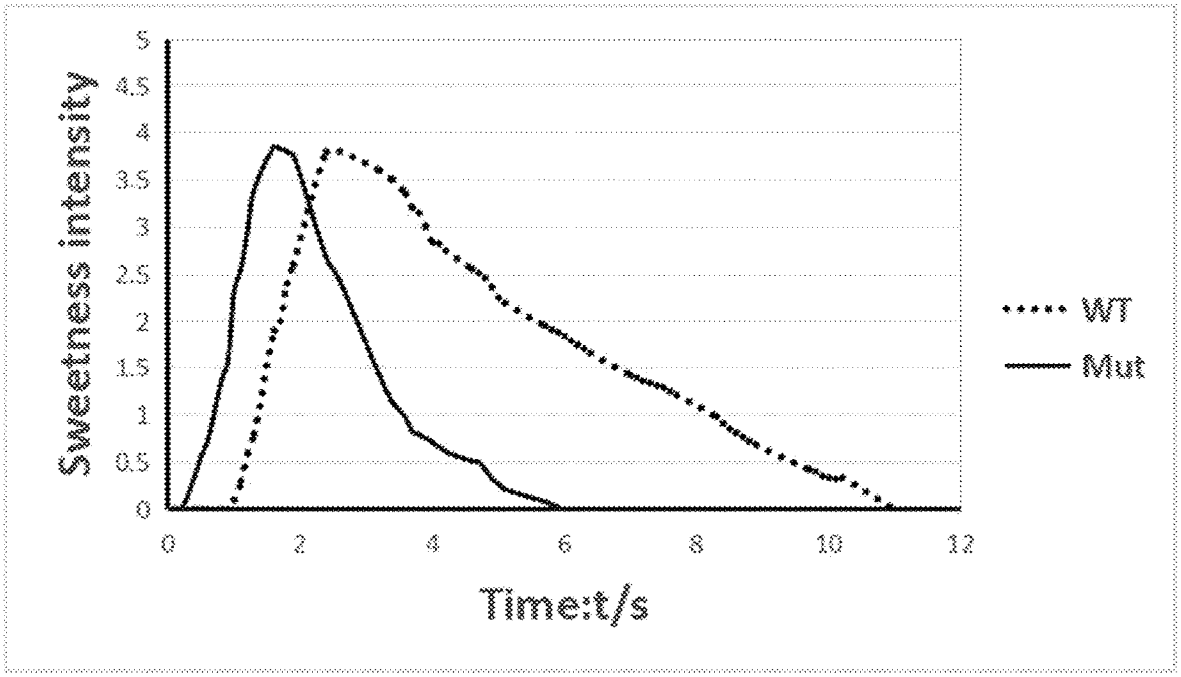
FIG. 14 is a schematic diagram illustrating an evaluation result of sweet taste perception kinetics on a K5D+V7R+D29N+A32K+N44E+E53R brazzein mutant solution and a WT protein solution according to some embodiments of the present disclosure.

The evaluation panel conducted an assessment on iso-sweet samples including the K5D+V7R+D29N+A32K+N44E+E53R brazzein mutant solution and the WT protein solution, both with distinctly perceptible sweet taste. The panelists rinsed the sample in their mouths for 5 seconds and then spit it out, and immediately recorded the changes in sweet taste intensity throughout the entire process from sample ingestion to the complete disappearance of sweet taste, so as to plot the time-intensity curves. As shown in FIG. 14, analysis of the key parameters—such as time to maximum intensity (T_max), maximum intensity (I_max), and extinction time (T_end, i.e., the time until the complete disappearance of sweet taste)—revealed that the WT protein solution exhibited a significant lag in the presentation of sweet taste. In contrast, the K5D+V7R+D29N+A32K+N44E+E53R brazzein mutant reached the peak of sweet taste perception more rapidly, with a significant reduction in sweet taste lag time; its sweet taste also faded more rapidly, yielding a fresher taste profile and effectively shortening the sweet taste residual time.

The present disclosure illustrates the sweet protein mutants, the preparation methods, and the use thereof with reference to the embodiments, but the present disclosure is not limited to the embodiments. That is, it does not mean that the present disclosure must rely on the embodiments to be implemented. Those skilled in the art should understand that any improvement to the present disclosure, equivalent replacement of various raw materials of the products of the present disclosure, addition of auxiliary ingredients, selection of specific implementations, etc., fall within the protection scope and disclosure scope of the present disclosure.

What is claimed is:

1. A brazzein mutant derived from a wild type brazzein having the amino acid sequence set forth in SEQ ID NO: 1, wherein the mutant possesses amino acid mutations relative to SEQ ID NO: 1 selected from the group consisting of:

(a) K5D, V7R, A32K, and N44E;

(b) D29N, A32K, N44E, and E53R; and (c) K5D, V7R, D29N, A32K, N44E, and E53R.

2. The brazzein mutant of claim 1, wherein the amino acid mutations are K5D, V7R, A32K, and N44E.

3. The brazzein mutant of claim 2, wherein the amino acid sequence of the brazzein mutant is set forth in SEQ ID NO: 29.

4. The brazzein mutant of claim 3, wherein the brazzein mutant is encoded by a nucleic acid having the sequence set forth in SEQ ID NO:30.

5. The brazzein mutant of claim 1, wherein the amino acid mutations are D29N, A32K, N44E, and E53R.

6. The brazzein mutant of claim 5, wherein the amino acid sequence of the brazzein mutant is set forth in SEQ ID NO: 31.

7. The brazzein mutant of claim 6, wherein the brazzein mutant is encoded by a nucleic acid having the sequence set forth in SEQ ID NO: 32.

8. The brazzein mutant of claim 1, wherein the amino acid mutations are K5D, V7R, D29N, A32K, N44E, and E53R.

9. The brazzein mutant of claim 8, wherein the amino acid sequence of the brazzein mutant is set forth in SEQ ID NO: 33.

10. The brazzein mutant of claim 9, wherein the brazzein mutant is encoded by a nucleic acid having the sequence set forth in SEQ ID NO: 34.

11. The brazzein mutant of claim 1, wherein at least one of bitter aftertaste, metallic flavor, astringent taste, and sweetness persistence of the brazzein mutant is less than that of the wild type brazzein.

12. The brazzein mutant of claim 1, wherein the brazzein mutant exhibits a reduced sweet taste lag time and a reduced sweet taste residual time compared to the wild type brazzein.

13. A nucleic acid molecule encoding the brazzein mutant of claim 1.

14. An expression vector comprising at least one copy of the nucleic acid molecule of claim 13.

15. A transformant comprising the expression vector of the claim 14, wherein the transformant is a genetically engineered cell that expresses the brazzein mutant of claim 1.

16. A method for preparing the brazzein mutant of claim 1, comprising:

constructing an expression vector, wherein the expression vector comprises at least one copy of a nucleic acid that encodes the brazzein mutant of claim 1;

constructing a transformant by transforming the expression vector into a recipient cell; and obtaining the brazzein mutant by culturing the transformant and collecting a culture.

17. The preparation method of claim 16, further comprising:

synthesizing a nucleic acid fragment encoding a wild type brazzein from a West African tropical plant *Pentadiplandra brazzeana* Baillon, the nucleic acid fragment having the sequence as set forth in SEQ ID NO: 2, and ligating the nucleic acid fragment into an expression vector via restriction enzyme digestion to obtain a recombinant plasmid; and performing site-directed mutagenesis using the recombinant plasmid as a template to obtain the expression vector comprising at least one copy of the nucleic acid that encodes the brazzein mutant.

18. A method for purifying the brazzein mutant of claim 1, comprising:

culturing a transformant comprising an expression vector comprising a nucleic acid that encodes the brazzein mutant of the claim 1 to collect a culture;

separating and removing contaminating proteins from the culture and then filtering the culture to obtain a filtered solution;

adsorbing the brazzein mutant from the filtered solution through a cation exchange resin, followed by eluting the resin to collect an eluent comprising the absorbed brazzein mutant;

performing nanofiltration on the eluent for desalination and concentration, and performing lyophilization on the nanofiltered eluent to obtain a purified brazzein mutant.

19. The purification method of claim 18, wherein the contaminating proteins are separated and removed from the culture via centrifugal separation.

* * * * *